United States Patent
Kohama

(10) Patent No.: US 8,278,397 B2
(45) Date of Patent: Oct. 2, 2012

(54) MEDICAL INSTRUMENT, MEDICAL MATERIAL, AND METHOD FOR PRODUCTION OF THE MEDICAL INSTRUMENT AND MEDICAL MATERIAL

(75) Inventor: Hiromasa Kohama, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/934,218

(22) PCT Filed: Mar. 23, 2009

(86) PCT No.: PCT/JP2009/055675
§ 371 (c)(1), (2), (4) Date: Sep. 23, 2010

(87) PCT Pub. No.: WO2009/119512
PCT Pub. Date: Oct. 1, 2009

(65) Prior Publication Data
US 2011/0054065 A1 Mar. 3, 2011

(30) Foreign Application Priority Data
Mar. 24, 2008 (JP) .................................. 2008-075866

(51) Int. Cl.
*C08G 63/91* (2006.01)
(52) U.S. Cl. ........ 525/411; 525/410; 525/415; 525/418; 525/419; 525/437; 525/440.01; 606/908; 606/910
(58) Field of Classification Search .................. 525/418, 525/419, 437, 440.01, 410, 411, 415; 528/272; 606/908, 910
See application file for complete search history.

(56) References Cited

U.S. PATENT DOCUMENTS

| | | | |
|---|---|---|---|
| 5,973,024 A | | 10/1999 | Imashiro et al. |
| 6,083,522 A | * | 7/2000 | Chu et al. ...................... 424/423 |
| 6,107,378 A | | 8/2000 | Imashiro et al. |
| 2002/0197296 A1 | * | 12/2002 | Gen .............................. 424/423 |
| 2003/0091646 A1 | | 5/2003 | Gen |

FOREIGN PATENT DOCUMENTS

| | | |
|---|---|---|
| JP | 2003-000695 A | 1/2003 |
| JP | 2004-204195 A | 7/2004 |
| JP | 3776578 B1 | 5/2006 |
| JP | 2006-137799 A | 6/2006 |

OTHER PUBLICATIONS

International Search Report (PCT/ISA/210) issued on May 12, 2009, by Japanese Patent Office as the International Searching Authority for International Application No. PCT/JP2009/055675.

Chun Lei Song et al., "Radiation Crosslinking of Biodegradable Poly(Butylene Succinate) At High Temperature", J. Macromol. Sci.—Pure Appl. Chem., A38 (9), pp. 961-971, (2001).

* cited by examiner

*Primary Examiner* — David W Wu
*Assistant Examiner* — Robert Jones, Jr.
(74) *Attorney, Agent, or Firm* — Buchanan Ingersoll & Rooney PC

(57) ABSTRACT

Disclosed are a medical instrument and a medical material each comprising an aliphatic polyester resin composition, which are hardly reduced in strength and impact resistance upon the sterilization by ionizing radiation or have excellent shape-retaining properties after a heat treatment. Specifically, a medical instrument and a medical material both sterilized by ionizing radiation are provided, each of which contains a biodegradable resin and a polycarbodiimide compound in an amount of 0.1 to 10% by weight on the resin. The biodegradable resin is polybutylene succinate, a copolymer of polybutylene succinate, or a mixture of polybutylene succinate and a copolymer of polybutylene succinate with polylactic acid or poly(3-hydroxyalkanoate). A method of producing such medical instrument and medical material is also provided.

2 Claims, No Drawings

MEDICAL INSTRUMENT, MEDICAL MATERIAL, AND METHOD FOR PRODUCTION OF THE MEDICAL INSTRUMENT AND MEDICAL MATERIAL

TECHNICAL FIELD

The present invention relates to medical instruments and medical materials composed of biodegradable resins. The medical instrument and medical material of the present invention are suitably used in the medical field, for instance. The present invention also relates to production methods for medical instruments and medical materials composed of biodegradable resins.

BACKGROUND ART

Medical instruments and medical materials are used in the situations where body fluid such as blood and urine may adhere to them, so that they should be made of plastics as a disposable article for single use, and their disposal needs to be carried out carefully by incineration or the like for the prevention of viral or bacterial infection. The use of such disposable instruments and materials, however, will increase waste, leading to an increase in carbon dioxide emitted by the incineration of waste.

Biodegradable resins are decomposed at the end of the product life cycle by microorganisms present in nature into carbon dioxide and water, imposing least burden on the environment. The biodegradable resins as such are expected to find wide application in various fields as a material for agriculture, a material for civil engineering and construction, or any other industrial material. Among others, those biodegradable resins which are made from plant-derived raw materials are also receiving attention from the viewpoint of global warming suppression for the reason that the carbon dioxide emitted during the disposal of such resins is to be absorbed by growing plants and, consequently, the total amount of carbon dioxide is not changed (carbon-neutral status).

Examples of the plant-derived biodegradable resins include polybutylene succinate as a flexible example, polylactic acid and poly(3-hydroxyalkanoate) as a relatively stiff example, as well as copolymers, blends and polymer alloys thereof.

Because of their reduced burden on the environment, biodegradable resins are very useful as a resin for use in the medical instruments and medical materials which are generally thrown away after being used one time.

Unfortunately, biodegradable resins are low in heat resistance, mechanical strength and moldability as compared with such general-purpose resins as polyethylene and polypropylene. It is necessary for an extensive, full-scale use of biodegradable resins to improve their physical properties through resin design, by addition of modifiers, and so forth.

Polybutylene succinate resins are the polyethylene-like resins of a flexible nature whose excellent impact resistance makes them suitable for parts of medical instruments. The polybutylene succinate resins can be made stiffer by mixing therein a polylactic acid resin or poly(3-hydroxyalkanoate) resin, so that the design for materials of a polybutylene succinate resin is easy to make in accordance with the intended use of the resin. It, however, is not possible to blend polylactic acid into a polybutylene succinate resin for the modification of the latter because the reduction in impact resistance due to the irradiation with ionizing radiation is an issue to be addressed for the polybutylene succinate resins also, and a considerable reduction occurs particularly in a resin having polylactic acid blended therein.

In addition, the polybutylene succinate resins have a melting point of about 110° C., which is lower than 115° C., the temperature as defined for the autoclave sterilization generally applied to medical instruments and medical materials. On a medical instrument and a medical material each composed of a polybutylene succinate resin alone or a mixture of a polybutylene succinate resin with a polylactic acid resin or poly(3-hydroxyalkanoate) resin, accordingly, the autoclave sterilization cannot be conducted due to a possible thermal distortion.

Ionizing radiation, as enabling sterilization approximately at normal temperatures, is suitable for the sterilization of less heat-resistant resins, but inappropriate to the sterilization of a medical instrument including a liquid such as an injection vessel, so that a heat-sterilizable resin is desired for such an instrument.

Crosslinking by means of the irradiation with ionizing radiation is disclosed as a technique for improving the heat resistance of polybutylene succinate (see Non-Patent Document 1, for instance). The ionizing radiation as used has an intensity of 210 kGy, so high an intensity as to inspire fears that the resin might be deteriorated.

Under the circumstances where the sterilization by ionizing radiation is frequently applied to medical instruments owing to its convenience, biodegradable resins are not used for medical instruments because the resins are considerably reduced in strength and impact resistance by the irradiation with ionizing radiation as compared with the general-purpose resins.

In a disclosed method of producing an ionizing radiation-sterilizable molded article of a biodegradable resin, a radiation crosslinker is added to a biodegradable resin, then the resin is sterilized by ionizing radiation (see Patent Document 1, for instance). During the irradiation with ionizing radiation, the radiation dose needs to be controlled in order to adjust the strength and the impact resistance of the resin as irradiated. Also disclosed is the technique for improving the hydrolysis resistance of a biodegradable resin that includes addition of polycarbodiimide as a terminal blocking agent (see Patent Document 2, for instance). It is not established yet whether or not the addition of polycarbodiimide to a biodegradable resin allows an inhibited reduction in strength and impact resistance during the sterilization by ionizing radiation.

Non-Patent Document 1: J. Macromol. Sci.—Pure Appl. Chem., A38(9), 961-971 (2001).
Patent Document 1: JP 2004-204195 A
Patent Document 2: JP 3776578 B

DISCLOSURE OF THE INVENTION

Problems to be Solved by the Invention

The present invention was made in view of the problems as above, aiming at providing a medical instrument and a medical material each using the aliphatic polyester resin composition which is less reduced in strength and impact resistance, or has an improved heat resistance, when treated at a radiation dose of 10 to 60 kGy employed in the sterilization by ionizing radiation.

Means to Solve the Problems

The inventors of the present invention found as a result of intensive researches that a biodegradable resin containing polycarbodiimide as a terminal blocking agent is less reduced in strength and impact resistance, or is made to have a heat resistance enabling autoclave sterilization, when irradiated with the ionizing radiation at a dose employed in the sterilization of medical instruments, and thus accomplished the invention.

The above aim is achieved according to the present invention as described in the following (1) through (5).

(1) A medical instrument and a medical material sterilized by ionizing radiation, each of which comprises a biodegradable resin and a polycarbodiimide compound in an amount of 0.1 to 10% by weight on the resin.

(2) The medical instrument and the medical material according to the above (1), wherein the biodegradable resin is polybutylene succinate, a copolymer of polybutylene succinate, or a mixture of polybutylene succinate and a copolymer of polybutylene succinate with polylactic acid or poly(3-hydroxyalkanoate).

(3) The medical instrument and the medical material according to the above (1) or (2), each of which comprises the polycarbodiimide compound in an amount of 0.5 to 5% by weight on the biodegradable resin.

(4) A method of producing a medical instrument and a medical material, comprising molding, then irradiating with ionizing radiation a composition containing a biodegradable resin and a polycarbodiimide compound in an amount of 0.1 to 10% by weight on the resin.

(5) The medical instrument and the medical material according to the above (4), wherein the biodegradable resin is polybutylene succinate, a copolymer of polybutylene succinate, or a mixture of polybutylene succinate and a copolymer of polybutylene succinate with polylactic acid or poly(3-hydroxyalkanoate).

(6) The medical instrument and the medical material according to the above (4) or (5), wherein the polycarbodiimide compound is contained in an amount of 0.5 to 5% by weight on the biodegradable resin.

Effects of the Invention

The addition of polycarbodiimide to a biodegradable resin has made it possible to provide the medical instrument and the medical material both as sterilized by ionizing radiation each of which is excellent in biodegradability, strength and impact resistance because the strength and the impact resistance of the resin before being sterilized by ionizing radiation can be maintained during the sterilization almost perfectly, or to provide the medical instrument and the medical material both as sterilized by ionizing radiation each of which is excellent in heat resistance. Since the strength and the impact resistance after the irradiation with the ionizing radiation for sterilization only slightly differ from those before the irradiation irrespective of the type or dose of the ionizing radiation in particular, the sterilization conditions can be specified in varying ways, and many types of medical instruments and materials can be provided, accordingly. The present invention thus has a very high versatility.

BEST MODE FOR CARRYING OUT THE INVENTION

The medical instrument and the medical material of the present invention will hereafter be described in detail.

The term "medical instrument" as used herein means an apparatus or instrument for use in the surgery, therapy or diagnosis performed on humans or animals, whose specific examples include those set forth in Ordinance for Enforcement of the Trademark Act, Appended Table (Ordinance of the Ministry of Economy, Trade and Industry, No. 202, 2001), Class 10 Section. The term "medical material" as used herein means the material for distribution or use of a medicinal agent or medical instrument that is to be disposed upon the use of the medicinal agent or medical instrument, such as a packaging material or accessory of a medicinal agent or medical instrument. The term "medicinal agent" as used herein means an agent for use in the surgery, therapy or diagnosis performed on humans or animals, whose specific examples include those set forth in the above Appended Table, Class 5 Section.

The term "ionizing radiation" as used herein means an electromagnetic wave or corpuscular radiation (beam) having an ionizing high energy, that is to say, the term is not concerned with radiations having non-ionizing low energies. The ionizing radiation is hereafter referred to simply as "radiation."

In the present invention, it is assumed that the strength is the yield stress as determined by tensile testing, and the impact resistance is the elongation at break as determined by tensile testing.

In the present invention, the heat resistance is to be understood as the resistance to the distortion after the storage at high temperatures.

The medical instrument and medical material (hereafter referred to as "medical instrument and the like") of the present invention are characterized in that they are each composed of the composition based on a biodegradable resin and containing polycarbodiimide that has a strength and an impact resistance both effectively maintained even after radiation irradiation, or is resistant to heat.

The biodegradable resin which is usable to the present invention is not particularly limited, with its examples including polybutylene succinate, a polybutylene succinate/adipate copolymer, a polybutylene succinate/carbonate copolymer, a polybutylene succinate/polylactic acid copolymer, poly(ε-caprolactone), polylactic acid, poly(3-hydroxyalkanoate) and a copolymer thereof, a polyethylene succinate/polybutylene succinate/terephthalate copolymer, a polybutylene adipate/terephthalate copolymer, a polytetramethylene adipate/terephthalate copolymer, a polybutylene succinate/adipate/terephthalate copolymer, as well as a polymer blend or polymer alloy of these resins.

The medical instrument and the like as radiation-sterilized which are excellent in strength and impact resistance are suitably obtained by using a polybutylene succinate resin having high flexibility and impact resistance, such as polybutylene succinate, a polybutylene succinate/adipate copolymer, a polybutylene succinate/carbonate copolymer and a polybutylene succinate/polylactic acid copolymer, as well as a polymer blend or polymer alloy of the polybutylene succinate resin and polylactic acid or poly(3-hydroxyalkanoate) of high strength. While a preferable mixing ratio of polylactic acid or poly(3-hydroxyalkanoate) depends on the product of interest and is not particularly limited, it is desirable to mix polylactic acid at a weight ratio of 0 to 50% on the polybutylene succinate resin. With amounts of polylactic acid over the upper limit, the resultant composition will increase in modulus of elasticity, and its use will be restricted.

The polycarbodiimide compound which is usable to the present invention may be produced in different ways, and may basically be produced by a conventional polycarbodiimide production method (U.S. Pat. No. 2,941,956; JP 47-33279 B; J. Org. Chem., 28, pp. 2069-2075, 1963; Chemical Review, Vol. 81, No. 4, pp. 619-621, 1981).

Examples of the organic diisocyanate as a material for the synthesis of the above polycarbodiimide compound include aromatic diisocyanates, aliphatic diisocyanates, alicyclic diisocyanates, and mixtures thereof, to be more specific, 1,5-naphthalene diisocyanate, 4,4'-diphenylmethane diisocyanate, 4,4'-diphenyldimethylmethane diisocyanate, 1,3-phenylene diisocyanate, 1,4-phenylene diisocyanate, 2,4-tolylene diisocyanate, 2,6-tolylene diisocyanate, a mixture of 2,4-tolylene diisocyanate and 2,6-tolylene diisocyanate, hexamethylene diisocyanate, cyclohexane-1,4-diisocyanate, xylylene diisocyanate, isophorone diisocyanate, dicyclohexylmethane-4,4'-diisocyanate, methylcyclohexane diisocyanate, tetramethylxylylene diisocyanate, 2,6-diisopropylphenyl isocyanate, and 1,3,5-triisopropylbenzene-2,4-diisocyanate.

The amount of the polycarbodiimide compound to be mixed in a biodegradable resin is preferably 0.1 to 10% by weight, especially 0.5 to 5% by weight, on the biodegradable resin. With amounts of less than 0.1% by weight, the mechanical strength-maintaining effect is not observed during the radiation sterilization and, on the other hand, amounts of more than 10 parts by weight may impair the physical properties of the biodegradable resin.

The biodegradable resin composition of the present invention may contain as required one or more conventional additives such as an antioxidant, a pigment, a softener, a plasticizer, a lubricant, an antistatic agent, an anti-fogging agent, a colorant, an oxidation inhibitor (aging inhibitor), a heat stabilizer, a light stabilizer, and an ultraviolet light absorber.

In the present invention, a polycarbodiimide compound may be mixed with a biodegradable resin by melt compounding on a twin-screw extruder, or the method may be used in which a polycarbodiimide compound is mixed into the biodegradable resin as already synthesized. It is also possible that a master batch of a biodegradable resin having a polycarbodiimide compound mixed therein is prepared in advance, and one or more other biodegradable resins are mixed with the master batch resin during the molding of a medical instrument. The molding method to be used is not particularly limited, with its examples including injection molding, extrusion, compression molding, and blow molding.

The medical instrument and the like of the present invention are sterilized by the irradiation with a radiation at a specified dose after, or in the process of, the molding into specified shapes, assembling, and packaging so as to allow their use as a medical instrument and the like. The dose of the radiation to be used for irradiation depends on the product of interest and is not particularly limited as long as it falls within the range of 5 to 100 kGy, with the preferred being a dose of 10 to 60 kGy.

The radiation to be used for irradiation may be an electron beam, γ-radiation, or X-rays. The electron beam generated by an electron accelerator and the γ-radiation from cobalt-60 are preferable because they facilitate industrial production, with the electron beam being more preferable. It is preferable that a medium- to high-energy electron accelerator with an acceleration voltage of 1 MeV or more is used in order to allow the inside of even a medical instrument and the like having thicker parts to be irradiated.

The atmosphere in which the radiation irradiation is conducted is not particularly limited, that is to say, the radiation irradiation may be conducted in an inert atmosphere with the air removed therefrom, or under vacuum. In addition, the irradiation may be conducted at any temperature, typically at room temperature.

While the heat resistance which is required of the medical instrument and the like of the present invention as radiation-sterilized depends on the shape of a medical instrument, the medical instrument and the like with a shape retention of 99% or higher after a storage at 120° C. for 30 minutes are considered as highly resistant to heat and excellent because of a less liability to distortion during autoclave sterilization.

The impact resistance which is required of the medical instrument and the like of the present invention as radiation-sterilized also depends on the shape of a medical instrument. A practical elongation at break as determined by tensile testing is 450% or higher, preferably 480% or higher, and more preferably 510% or higher, and the medical instrument and the like with an elongation at break of 450% or higher are considered as highly resistant to impact and functionally excellent because of a less liability to breakage due to the impact during transport or upon dropping.

The strength which is required of the medical instrument and the like of the present invention as radiation-sterilized also depends on the shape of a medical instrument. A practical yield stress as determined by tensile testing is 26 MPa or higher, preferably 28 MPa or higher, and more preferably 30 MPa or higher, and the medical instrument and the like with a yield stress value not smaller than the upper limit are considered as high in strength and functionally excellent because of a less liability to breakage even in the form of a thin sheet.

In the present invention, the medical instrument and the like are exemplified by a container for agents, a syringe filled with an injection, a disposable syringe, a container for injection needles, a catheter tube, a transfusion tube, a stopcock, tray, a nonwoven fabric, surgical gloves, a gown, a sheet, and a filter.

The present invention will be illustrated with reference to Examples as below, although not limited thereto.

Example 1

(1) Preparation of Polycarbodiimide Master Batch

By mixing 22.5 kg of polybutylene succinate (GS Pla AZ81T manufactured by Mitsubishi Chemical Corporation) and 2.5 kg of CARBODILITE LA-1 (manufactured by Nisshinbo Chemical Inc.) as polycarbodiimide, the composition was obtained in which the two components were homogeneously mixed together. The composition was subjected to melt compounding at a temperature of 180° C. using a twin-screw extruder (LABO PLASTOMILL manufactured by Toyo Seiki Seisaku-sho, Ltd.), then pelletized to obtain 25 kg of a polycarbodiimide master batch (polycarbodiimide content, 10% by weight).

(2) Preparation of Polycarbodiimide-Containing Resin

A mixture obtained by mixing 1.6 kg of polybutylene succinate (GS Pla AZ81T manufactured by Mitsubishi Chemical Corporation) and 0.4 kg of the polycarbodiimide master batch as prepared in the above (1) was subjected to melt compounding at a temperature of 190° C. using a twin-screw extruder (LABO PLASTOMILL manufactured by Toyo Seiki Seisaku-sho, Ltd.), then pelletized to obtain 1.8 kg of a polycarbodiimide-containing resin (polycarbodiimide content, 2% by weight).

(3) Making of Sheet of Polycarbodiimide-Containing Resin

The polycarbodiimide-containing resin as prepared in the above (2) (polycarbodiimide content, 2% by weight) was pressed with a pressure of 20 MPa at a temperature of 200° C. using a bench-scale hot press (type SA-303 manufactured by TESTER SANGYO CO., LTD.), then quenched to mold it in the form of a sheet 150 mm wide, 150 mm long and 0.5 mm thick as a tray material sheet.

(4) Radiation Irradiation

The sheet as obtained in the above (3) was irradiated at room temperature with 55 kGy of electron beam from a 10-MeV electron accelerator to provide the tray material sheet as radiation-irradiated.

Example 2

The tray material sheet as radiation-irradiated was provided by following the procedure in Example 1 except that the raw material resins as used in (2) were 1.5 kg of polybutylene succinate (GS Pla AZ81T manufactured by Mitsubishi Chemical Corporation), 0.1 kg of polylactic acid (LACEA H-100 manufactured by Mitsui Chemicals, Inc.), and 0.4 kg of the polycarbodiimide master batch.

Example 3

The tray material sheet as radiation-irradiated was provided by following the procedure in Example 1 except that the raw material resins as used in (2) were 1.4 kg of polybutylene succinate (GS Pla AZ81T manufactured by Mitsubishi Chemical Corporation), 0.2 kg of polylactic acid (LACEA H-100 manufactured by Mitsui Chemicals, Inc.), and 0.4 kg of the polycarbodiimide master batch.

Example 4

The tray material sheet as radiation-irradiated was provided by following the procedure in Example 1 except that the raw material resins as used in (2) were 1.3 kg of polybutylene succinate (GS Pla AZ81T manufactured by Mitsubishi Chemical Corporation), 0.3 kg of polylactic acid (LACEA H-100 manufactured by Mitsui Chemicals, Inc.), and 0.4 kg of the polycarbodiimide master batch.

Example 5

The tray material sheet as radiation-irradiated was provided by following the procedure in Example 1 except that the raw material resins as used in (2) were 1.2 kg of polybutylene succinate (GS Pla AZ81T manufactured by Mitsubishi Chemical Corporation), 0.4 kg of polylactic acid (LACEA H-100 manufactured by Mitsui Chemicals, Inc.), and 0.4 kg of the polycarbodiimide master batch.

Example 6

The tray material sheet as radiation-irradiated was provided by following the procedure in Example 1 except that the raw material resins as used in (2) were 1.1 kg of polybutylene succinate (GS Pla AZ81T manufactured by Mitsubishi Chemical Corporation), 0.5 kg of polylactic acid (LACEA H-100 manufactured by Mitsui Chemicals, Inc.), and 0.4 kg of the polycarbodiimide master batch.

Example 7

The tray material sheet as radiation-irradiated was provided by following the procedure in Example 1 except that the raw material resins as used in (2) were 0.7 kg of polybutylene succinate (GS Pla AZ81T manufactured by Mitsubishi Chemical Corporation), 0.5 kg of polylactic acid (LACEA H-100 manufactured by Mitsui Chemicals, Inc.), and 0.8 kg of the polycarbodiimide master batch.

Comparative Example 1

The tray material sheet as radiation-irradiated was provided by following the procedure in Example 1 except that 1 kg of polybutylene succinate (GS Pla AZ81T manufactured by Mitsubishi Chemical Corporation) was used in (2) as a sole raw material resin.

Comparative Example 2

The tray material sheet as radiation-irradiated was provided by following the procedure in Example 1 except that the raw material resins as used in (2) were 1.5 kg of polybutylene succinate (GS Pla AZ81T manufactured by Mitsubishi Chemical Corporation) and 0.5 kg of polylactic acid (LACEA H-100 manufactured by Mitsui Chemicals, Inc.).

Comparative Example 3

A mixture obtained by mixing 1.5 kg of polybutylene succinate (GS Pla AZ81T manufactured by Mitsubishi Chemical Corporation), 0.5 kg of polylactic acid (LACEA H-100 manufactured by Mitsui Chemicals, Inc.), and 0.04 kg of bis(2,6-diisopropylphenyl)carbodiimide (manufactured by TOKYO CHEMICAL INDUSTRY CO., LTD.) was subjected to melt compounding at a temperature of 190° C. using a twin-screw extruder (LABO PLASTOMILL manufactured by Toyo Seiki Seisaku-sho, Ltd.), then pelletized to obtain 1.8 kg of a carbodiimide-containing resin (carbodiimide content, 2% by weight). Thereafter, the tray material sheet as radiation-irradiated was provided by following the procedure in (3) and (4) of Example 1.

Example 8

Four tray material sheets were made by following the procedure in (1) through (3) of Example 1 except that the raw material resins as used (2) were 1.8 kg of polybutylene succinate (GS Pla AZ81T manufactured by Mitsubishi Chemical Corporation) and 0.2 kg of the polycarbodiimide master batch. The tray material sheets as obtained were irradiated at room temperature with 20 kGy and 40 kGy of electron beams from a 10-MeV electron accelerator as well as 20 kGy and 40 kGy of γ-radiations from cobalt-60, respectively, to provide four different tray material sheets as radiation-irradiated.

Example 9

The tray material sheets as radiation-irradiated were provided by following the procedure in Example 8 except that the raw material resins as used in (2) were 1.6 kg of polybutylene succinate (GS Pla AZ81T manufactured by Mitsubishi Chemical Corporation) and 0.4 kg of the polycarbodiimide master batch.

Example 10

The tray material sheets as radiation-irradiated were provided by following the procedure in Example 8 except that the raw material resins as used in (2) were 1.4 kg of polybutylene succinate (GS Pla AZ81T manufactured by Mitsubishi Chemical Corporation) and 0.6 kg of the polycarbodiimide master batch.

Example 11

The tray material sheets as radiation-irradiated were provided by following the procedure in Example 8 except that the raw material resins as used in (2) were 1.2 kg of polybutylene succinate (GS Pla AZ81T manufactured by Mitsubishi Chemical Corporation) and 0.8 kg of the polycarbodiimide master batch.

(Evaluation 1)
(Tensile Test)

Out of the tray material sheets as made in Examples 1 to 11 and Comparative Examples 1 to 3, 5B-type dumbbell specimens defined in ISO 527-2 were cut with a die. Using an Autograph testing machine (type AG-IS manufactured by SHIMADZU CORPORATION), the specimens were subjected to a tensile test at a test rate of 10 mm/min. so as to measure the tensile yield stress and the elongation at break.

Measurements are set forth in Tables 1 and 2. It was confirmed that addition of polycarbodiimide allowed the tensile yield stress and the elongation at break after radiation irradiation to less differ from those before radiation irradiation, and allowed the strength and the impact resistance after irradiation to only slightly differ from those before irradiation irrespective of the type or dose of the radiation. It was thus confirmed that properties of the materials as prepared in Examples, such as the tensile yield stress and the elongation at break, would not change significantly due to radiation sterilization, so that the materials of Examples were demonstrated to be available to various types of medical instrument and the like.

TABLE 1

Tensile Test Results (Irradiation with 55 kGy of electron beam)

| | Yield stress (MPa) | | | Elongation at break (%) | | |
|---|---|---|---|---|---|---|
| | Non-irradiated | Irradiated | Rate of change (%) | Non-irradiated | Irradiated | Rate of change (%) |
| Ex. 1 | 35 | 35 | 102 | 850 | 770 | 90 |
| Ex. 2 | 35 | 35 | 100 | 840 | 750 | 90 |
| Ex. 3 | 36 | 36 | 101 | 750 | 720 | 96 |
| Ex. 4 | 38 | 36 | 97 | 700 | 690 | 99 |
| Ex. 5 | 38 | 37 | 97 | 660 | 670 | 101 |
| Ex. 6 | 39 | 39 | 100 | 620 | 620 | 99 |
| Ex. 7 | 35 | 35 | 100 | 540 | 510 | 94 |
| Comp. Ex. 1 | 31 | 33 | 107 | 910 | 440 | 48 |
| Comp. Ex. 2 | 37 | 38 | 103 | 540 | 340 | 63 |
| Comp. Ex. 3 | 35 | 34 | 99 | 490 | 270 | 55 |

Rate of change: Value obtained by dividing the value of irradiated specimen by the value of non-irradiated specimen.

TABLE 2

Tensile Test Results

| | Type and dose of radiation | Yield stress (MPa) | | | Elongation at break (%) | | |
|---|---|---|---|---|---|---|---|
| | | Non-irradiated | Irradiated | Rate of change (%) | Non-irradiated | Irradiated | Rate of change (%) |
| Ex. 8 | 20 kGy EB | 33 | 35 | 104 | 910 | 810 | 88 |
| | 40 kGy EB | | 34 | 103 | | 520 | 57 |
| | 20 kGy γ-radiation | | 36 | 109 | | 880 | 96 |
| | 40 kGy γ-radiation | | 37 | 112 | | 840 | 92 |
| Ex. 9 | 20 kGy EB | 34 | 35 | 104 | 910 | 900 | 99 |
| | 40 kGy EB | | 35 | 103 | | 820 | 90 |
| | 20 kGy γ-radiation | | 37 | 108 | | 870 | 96 |
| | 40 kGy γ-radiation | | 37 | 110 | | 770 | 85 |
| Ex. 10 | 20 kGy EB | 34 | 35 | 104 | 920 | 910 | 99 |
| | 40 kGy EB | | 36 | 105 | | 840 | 91 |
| | 20 kGy γ-radiation | | 37 | 107 | | 900 | 98 |
| | 40 kGy γ-radiation | | 38 | 110 | | 730 | 79 |
| Ex. 11 | 20 kGy EB | 33 | 34 | 101 | 870 | 870 | 101 |
| | 40 kGy EB | | 36 | 109 | | 790 | 92 |
| | 20 kGy γ-radiation | | 37 | 111 | | 730 | 84 |
| | 40 kGy γ-radiation | | 38 | 114 | | 740 | 86 |

Rate of change: Value obtained by dividing the value of irradiated specimen by the value of non-irradiated specimen.

Example 12

The tray material sheet as radiation-irradiated was provided by following the procedure in Example 1 except that the raw material resins as used in (2) were 1.0 kg of polybutylene succinate (GS Pla AZ81T manufactured by Mitsubishi Chemical Corporation), 0.6 kg of polylactic acid (LACEA H-100 manufactured by Mitsui Chemicals, Inc.), and 0.4 kg of the polycarbodiimide master batch.

Example 13

The tray material sheet as radiation-irradiated was provided by following the procedure in Example 1 except that the raw material resins as used in (2) were 0.8 kg of polybutylene succinate (GS Pla AZ81T manufactured by Mitsubishi Chemical Corporation), 0.8 kg of polylactic acid (LACEA H-100 manufactured by Mitsui Chemicals, Inc.), and 0.4 kg of the polycarbodiimide master batch.

Example 14

The tray material sheet as radiation-irradiated was provided by following the procedure in Example 1 except that the raw material resins as used in (2) were 0.6 kg of polybutylene succinate (GS Pla AZ81T manufactured by Mitsubishi Chemical Corporation), 1.0 kg of polylactic acid (LACEA H-100 manufactured by Mitsui Chemicals, Inc.), and 0.4 kg of the polycarbodiimide master batch.

Comparative Example 4

The tray material sheet as radiation-irradiated was provided by following the procedure in Example 1 except that the raw material resins as used in (2) were 0.4 kg of polybutylene succinate (GS Pla AZ81T manufactured by Mitsubishi Chemical Corporation) and 1.2 kg of polylactic acid (LACEA H-100 manufactured by Mitsui Chemicals, Inc.).

Example 15

The tray material sheet as radiation-irradiated was provided by following the procedure in Example 1 except that the raw material resins as used in (2) were 1.1 kg of polybutylene succinate (GS Pla AZ81T manufactured by Mitsubishi Chemical Corporation), 0.5 kg of poly(3-hydroxyalkanoate) (polyhydroxybutyrate/valerate manufactured by Hayashi Corporation), and 0.4 kg of the polycarbodiimide master batch.

Example 16

The tray material sheet as radiation-irradiated was provided by following the procedure in Example 1 except that the raw material resins as used in (2) were 0.6 kg of polybutylene succinate (GS Pla AZ81T manufactured by Mitsubishi Chemical Corporation), 1.0 kg of poly(3-hydroxyalkanoate) (polyhydroxybutyrate/valerate manufactured by Hayashi Corporation), and 0.4 kg of the polycarbodiimide master batch.

Comparative Example 5

The tray material sheet as radiation-irradiated was provided by following the procedure in Example 1 except that the raw material resins as used in (2) were 0.4 kg of polybutylene succinate (GS Pla AZ81T manufactured by Mitsubishi Chemical Corporation), 1.2 kg of poly(3-hydroxyalkanoate) (polyhydroxybutyrate/valerate manufactured by Hayashi Corporation), and 0.4 kg of the polycarbodiimide master batch.

(Evaluation 2)
(Heat Resistance Test)

Out of the tray material sheets as provided in Examples 1, 5 and 12 to 16 as well as Comparative Examples 4 and 5, specimens (50 mm long and 10 mm wide each) were cut. The specimens were left in an oven at 120° C. for 30 minutes, then removed from the oven and cooled to room temperature. The length of each specimen was measured before and after the heat treatment to calculate the shape retention (%) [(length after heat treatment)/(length before heat treatment)×100]. For the purpose of comparison, the specimens which were obtained from the sheets before radiation irradiation were also evaluated in a similar manner.

Calculated values are set forth in Table 3. It was confirmed that each of the radiation-irradiated specimens composed of polybutylene succinate or a polybutylene succinate mixture had a shape retention of 99% or higher, that is to say, was likely to maintain its shape and, consequently, high in heat resistance. This applied to both the specimens containing polylactic acid (Examples 1, 5 and 12 to 14) and those containing poly(3-hydroxyalkanoate) (Examples 15 and 16). In the case of non-irradiated specimens, the heat resistance was low, and the shape retention was lower as the polybutylene succinate content was higher.

The effect of radiation irradiation was not indicated on the specimens with a polybutylene succinate content of 40% or lower because such specimens avoided a significant distortion even when not irradiated with a radiation (Comparative Examples 4 and 5).

TABLE 3

| | Shape Retention (%) after Treatment at 120° C. | |
|---|---|---|
| | Irradiated specimen | (Non-irradiated specimen) |
| Example 1 | 99.0 | (90.8) |
| Example 5 | 99.3 | (97.6) |
| Example 12 | 99.0 | (98.1) |
| Example 13 | 99.4 | (98.1) |
| Example 14 | 99.0 | (98.7) |
| Example 15 | 99.0 | (98.3) |
| Example 16 | 99.5 | (98.9) |
| Comp. Example 4 | 99.4 | (99.4) |
| Comp. Example 5 | 99.7 | (99.9) |

The invention claimed is:

1. A medical instrument or a medical material sterilized by ionizing radiation, which comprises a biodegradable resin and a polycarbodiimide compound in an amount of 1 to 4% by weight on the resin, wherein said biodegradable resin is a mixture of polybutylene succinate and polylactic acid or poly (3-hydroxyalkanoate).

2. A method of producing a medical instrument or a medical material, comprising molding, then irradiating with ionizing radiation a composition containing a biodegradable resin and a polycarbodiimide compound in an amount of 1 to 4% by weight on the resin, wherein said biodegradable resin is a mixture of polybutylene succinate and polylactic acid or poly(3-hydroxyalkanoate).

* * * * *